US012582502B1

(12) United States Patent　　　　　(10) Patent No.:　US 12,582,502 B1

Schofield et al.　　　　　　　　　　　(45) Date of Patent:　　Mar. 24, 2026

(54) DETACHABLE CANISTERS FOR USE WITH DENTAL AMALGAM SEPARATION AND RECYCLING SYSTEMS

(71) Applicant: Solmetex LLC, Northborough, MA (US)

(72) Inventors: Robin Schofield, Lancaster, MA (US); Richard Goulston, Stuart, FL (US); Edward M Morassi, Chelmsford, MA (US); Nick Mozzicato, Acton, MA (US)

(73) Assignee: Solmetex LLC, Northborough, MA (US)

( * ) Notice: Subject to any disclaimer, the term of this patent is extended or adjusted under 35 U.S.C. 154(b) by 302 days.

(21) Appl. No.: 18/117,366

(22) Filed: Mar. 3, 2023

Related U.S. Application Data

(60) Provisional application No. 63/317,129, filed on Mar. 7, 2022.

(51) Int. Cl.
　　*A61C 5/66*　　　(2017.01)
　　*A61C 17/06*　　(2006.01)
　　*A61M 1/00*　　(2006.01)

(52) U.S. Cl.
　　CPC .............. *A61C 5/66* (2017.02); *A61C 17/065* (2019.05); *A61M 1/88* (2021.05)

(58) Field of Classification Search
　　CPC .......... A61C 5/66; A61C 17/065; A61M 1/88
　　See application file for complete search history.

(56) References Cited

U.S. PATENT DOCUMENTS 4,385,891 A　*　5/1983　Ligotti ................. A61C 17/065
　　　　　　　　　　　　　　　　　　433/92

* cited by examiner

*Primary Examiner* — Thuan D Dang

(57)　　　　　　　ABSTRACT

The present invention provides detachable canisters for use with dental amalgam recycling systems, useful for recycling particles drawn from dental liquid effluent, for example, using a dental amalgam recycling apparatus using an air-water separation tank.

9 Claims, 11 Drawing Sheets

24

26

25

27

27

Tapered Sealing Surface

[Section  A-A]

Flat Sealing Surface

Section A-A

OverMolded Sealing Surface

[Section A-A]

DETACHABLE CANISTERS FOR USE WITH DENTAL AMALGAM SEPARATION AND RECYCLING SYSTEMS

FIELD OF THE INVENTION

This invention relates to improved systems and apparatus for the removal recovery and potential recycling of particles removed from effluent waste, and particularly, to improved canisters for use with dental amalgam separation and recycling systems to remove amalgam and other metallic particles and other abrasive solids from dental office suction effluent. The improved canisters can be used with existing dental amalgam separation and recycling apparatus that are presently in use, and serves as a self-contained recycling container to facilitate customer regulatory compliance and environmental safeguards.

BACKGROUND OF THE INVENTION

Dental amalgam is a dental filling material used to fill cavities caused by tooth decay. It has been used for more than 150 years in hundreds of millions of patients around the world.

Dental amalgam is a mixture of metals, consisting of liquid (elemental) mercury and a powdered alloy composed of silver, tin, and copper. Approximately 50% of dental amalgam is elemental mercury by weight. The chemical properties of elemental mercury allow it to react with and bind together the silver/copper/tin alloy particles to form an amalgam. See www.fda.gov/MedicalDevices/Productsand-Medical Procedures/DentalProducts/DentalAmalgam/ucm171094.htm, accessed Sep. 9, 2016.

Amalgam is used less often than in the past, mostly because tooth-colored materials now can be used. However, the newer materials can't be used for all dental situations, amalgam is less costly than newer materials and it lasts longer, especially in teeth that undergo a lot of pressure and wear from chewing.

Better dental health overall coupled with increased demand for more modern alternatives such as resin composite fillings (which match the tooth color), as well as public concern about the mercury content of dental amalgam, have resulted in a steady decline in dental amalgam use in developed countries, though overall amalgam use continues to rise worldwide. Stein, P S; Sullivan, J; Haubenreich, J E; Osborne, P B (2005). "Composite resin in medicine and dentistry." Journal of long-term effects of medical implants. 15 (6): 641-54. doi:10.1615/jlongtermeffmedimplants. v15.16.70. PMID 16393132.

Although amalgams are less frequently used in developed countries for new dental fillings than in the past, amalgams continue to make up a portion of the particle component of dental office effluent mainly because of the fact that old fillings made of amalgams are drilled out and removed in the effluent waste when new fillings are effected to replace the old. Further, as noted above, even under current dental practice, an amalgam is preferred for some tooth filling situations.

Because mercury is a poison that can accumulate in living tissues and can pose a health hazard to species in a food chain exposed to mercury-containing compounds, and since humans are inevitably at the end of the food chain, it follows that effluent containing amalgams can pose a health hazard to the community at large. Also, certain metals such as silver are commercially valuable if recovered in quantity. For those reasons, it is desirable to devise systems, apparatus and processes for removing amalgams from dental office effluent and efficiently recycling those amalgams.

In addition to removing amalgams, other matter disposed into dental office suction effluent includes aluminum oxides used in air abrasion treatments and other solid waste material. These solid materials tend to wear out or damage vacuum pumps and other equipment downstream of the dental chair suction apparatus, and also constitute effluent water contaminants. Therefore, it is desirable for the apparatus to remove solid abrasive material and other particulate waste from the dental office suction effluent.

The World Health Organization also points out that amalgam separators, installed in the waste water lines of many dental offices, dramatically decrease the release of mercury into the public sewer system. However, critics say that the separators are still not mandatory in some states of the United States. "Purchasing, installing and operating dental amalgam separators: Practical issues". The Journal of the American Dental Association. 134 (8): 1054-65. doi: 10.14219/jada.archive.2003.0319. PMID 12956345. Recently, the EPA has proposed nation-wide regulations requiring separators and it is scheduled to come into force in 2016.

Previously known apparatus for removing amalgam particles from dental office suction effluent are known to include a collecting tank for collecting a day's accumulation of suction effluent from one or more sources of such waste. The waste is sucked from the dental chair suction apparatus and into the collecting tank by a vacuum pump. When the vacuum pump is turned off, an outlet valve is opened and the accumulated waste is deposited into a separation device intended to separate metal particles from the effluent liquid. Flow into the separation device is induced by the head of fluid in the collecting tank. Particles passing through the separation device are separated from the waste by gravity and settle to the bottom of the separation device. The flow rate is dependent on the head inside the collecting tank; as the head diminishes, the flow rate also diminishes. The changes in flow rate are undesirable because the particle separation rate is affected, and the system becomes prone to plugging when the flow rate decreases. Also, since the waste can be deposited only when the vacuum pump is off, waste is usually moved to the separation device at the end of the day. As a result, the collecting tank and separation device tend to be undesirably large and the whole process is time consuming.

Another known apparatus is a centrifuge type system that separates heavier metal particles from effluent liquid by collecting the particles at the peripheral wall of the centrifuge. This apparatus does not effectively separate lighter particles, and is expensive to purchase and operate due to the complexity of its mechanical parts.

Yet another known apparatus uses a dedicated mechanical pump to suction waste liquids through a separator device. Again, a dedicated pump can be expensive to purchase and to maintain, and can be undesirably space-consuming.

Such known systems can become quite complex, unwieldy and expensive, as for example that disclosed in U.S. Pat. No. 5,885,076 granted 23 Mar. 1999. It teaches the use of sedimentation, co-precipitation and filtration in an expensive complicated apparatus that is probably economical, if at all, only for relatively large installations such as a military base dental complex.

U.S. Pat. Nos. 6,692,636 and 6,596,754 are patents that disclose systems for removing amalgam from dental office suction effluent.

After collecting the amalgam and other solid waste the dentist is left with the problem of what to do with the waste. Either the dentist has to deal with his own hazardous waste of he can send his collected material to a recycler. In either case, the "collection container" needs to be disposable and easily replaceable.

Existing recycling programs generally require the provision of bulky shipping materials and the delivery of those materials to the dentist for every full container. If such materials are not provided and the materials are not properly recycled a large part of the benefit of collecting the amalgam waste can be lost. It is important that the waste is recycled under federal guidelines in order to make sure the full benefits of amalgam separation are achieved.

Additionally, containers for collection, such as dental amalgam recycling systems, can be compromised by incorrect installation or misalignment, which can cause O-rings to deform and/or seal irregularly, and result in leakage.

The present inventors have gained significant experience working with newer dental amalgam separation systems, including the Solmetex® [Legacy] Hg5® Amalgam Separator and the Solmetex® NXT Hg5 Amalgam Separator systems, for example, as described in U.S. Pat. No. 10,646, 313; United States Patent Application No. 2018/338822; and PCT Application No. WO 2018/071615, the entire disclosure of each of these documents is hereby incorporated herein by reference.

SUMMARY OF THE INVENTION

The present invention provides canisters that are compatible with dental amalgam separation systems, in particular, the Solmetex NXT Hg5 Amalgam Separator systems, and provide solutions for the problem of providing compatible canisters that are relatively easy to install and to remove. The canisters provide options for the mode of canister replacement, providing for air- and water-tight seal, with correctly aligned installation and removal; and provide further advantages that will be apparent after reviewing the following detailed description.

The present inventors realized that the combination and alignment of features present on the mating surface of a detachable canister or container could provide significant advantages when they are designed for installation with a dental amalgam separator system, such as the Solmetex NXT Hg5 Amalgam Separator System, designed with a reciprocal combination and alignment of features on the air-water separator tank surface that is designed to mate with and attach to the container.

The skilled artisan will readily recognize that the container inlet port and container outlet port are asymmetrically aligned along a central axis across the diameter of the top mating surface. This alignment of the container inlet port and container outlet port, with one port, preferably the container inlet port, closer to the center of the top mating surface, and the other port, preferably the container outlet port, closer to the outside of the top mating surface, results in an optimal fit and secure attachment of the detachable container to a dental amalgam separator apparatus where the dental amalgam air-water separating tank has a reciprocal arrangement of features to accommodate the detachable container. The asymmetrical alignment of the ports on the top mating surface provides a unique optimal alignment of the detachable container to match the reciprocal arrangement of features of the dental amalgam air-water separator tank. This minimizes or eliminates the possibility that the detachable container will be incorrectly installed with a mismatched alignment, and effectively ensures correct attachment. The additional features that are described— including but not limiting the use and positioning of O-rings and O-ring grooves, or the shape and/or size of the inlet and outlet ports, serve to minimize or eliminate a loose or incomplete seal, and significantly reduce or eliminate leakage from the apparatus in operation, as well as during installation or replacement of the detachable container.

In one aspect, the invention comprises a detachable container useful as a dental amalgam recycling container, said detachable container having an outside top mating surface comprising a container inlet port and a container outlet port, wherein each of the container inlet port and container outlet port comprise an O-ring fitted in an O-ring groove (24) to prevent leaks, wherein the O-rings are located at different heights, allowing for the container inlet port to form an air-tight and water-tight seal with an air-water separator tank liquid effluent outlet and for the container outlet port to form an air-tight and water-tight seal with a further conduit means for liquid effluent discharge after solid amalgams have separated from the liquid effluent and collected in the detachable container. The container inlet and container outlet port themselves may be of the same height, in which case the O-ring groove is preferably located lower on the container inlet port [See FIG. 6]. In other embodiments, the container inlet and container outlet port themselves may be of different heights, in which case, the container inlet port is preferably lower in height than the container inlet port, and the O-ring groove (24) may be located equally distant from the top of each of the ports [See FIG. 10A].

In another aspect, the invention comprises a detachable container useful as a dental amalgam recycling container, said detachable container having an outside top mating surface comprising a container inlet port and a container outlet port, wherein each of the container inlet port and container outlet port are of the same height, and one of the ports, preferably the container inlet port, comprises a stepped diameter. That is, the port, preferably the container inlet port, comprises a lower portion (25) that comprises a first diameter, and an upper portion (26) that comprises a second diameter, the second diameter being smaller than the first diameter. Both ports preferably comprise an O-ring fitted in an O-ring groove to prevent leaks. The O-ring groove (24) is preferably located near the top of the container outlet port, and the O-ring on the container inlet port is preferably located near the top of the lower portion (25), such that the upper portion (26) is located just above O-ring groove located on the lower portion [See FIG. 7].

In other embodiments, the invention comprises a detachable container useful as a dental amalgam recycling container, said detachable container having an outside top mating surface comprising a container inlet port and a container outlet port, wherein each of the container inlet port and container outlet port are of the same height, and one of the ports, preferably the container inlet port, comprises a tapered diameter. That is, the port comprising a tapered diameter, preferably the container inlet port, comprises a lower portion (25) that comprises a first diameter, and an upper portion (26) that is tapered so that the bottom of the upper portion comprises a diameter equal to the first diameter, and the diameter narrows gradually from the bottom of the upper portion to the top of the upper portion, which has a second diameter, the second diameter being smaller than the first diameter. Both ports preferably comprise an O-ring fitted in an O-ring groove to prevent leaks. The port comprising a tapered diameter, comprises an O-ring fitted in an O-ring groove to prevent leaks, with the O-ring groove preferably being located near the top of the container outlet port, and the O-ring on the container inlet port preferably being located near the top of the lower portion, such that the upper portion begins just above O-ring groove located at the top of the lower portion [See FIG. 8]. Alternatively, the ports can be of different heights, in which case the container inlet port is preferably shorter.

In other embodiments the invention comprises a detachable container useful as a dental amalgam recycling container, said detachable container having an outside top mating surface comprising a container inlet port and a container outlet port. The outer rim of the outside top mating surface comprises two tabs (27) projecting outward from the container, the tabs being located opposite from each other along the outer rim [FIG. 9]. The detachable container can be attached to an air-water separator tank of a dental amalgam separator apparatus when the container inlet port and container outlet port are aligned with an air-water separator tank liquid effluent outlet and with further conduit means for liquid effluent discharge, respectively. After proper alignment, the detachable container is attached to the air-water separator tank, and the detachable container may be further secured in place using two retaining pins (13).

The tabs provide a surface or ridge under which retaining pins may be placed to add to the security of the detachable container. One retaining pin is inserted just below each of the tabs projecting outward from the container, into an accommodating hole or slot located on the dental amalgam separator apparatus, for example, at or near the bottom or lower surface of an air-water separation tank, thus ensuring that the detachable container does not unintentionally detach from the air-water separation tank when there is no vacuum in the system. The tabs may comprise a larger or smaller proportion of the outside top mating surface. The retaining pins and tabs should preferably be of sufficient rigidity and strength so that they are able to support the weight of the detachable container when filled.

In other aspects, the invention comprises a detachable container useful as a dental amalgam recycling container, said detachable container having an outside top mating surface comprising a container inlet port and a container outlet port, wherein each of the container inlet port and container outlet port comprises a tapered sealing surface, such that, when the detachable container is aligned with and attached to an air-water separating tank of an amalgam separation apparatus, the tapered sealing surface of the container inlet port forms an air-tight and water-tight seal with an air-water separator tank liquid effluent outlet and for the tapered sealing surface of the container outlet port forms an air-tight and water-tight seal with a further conduit means for liquid effluent discharge after solid amalgam has separated from the liquid effluent and collected at the bottom of the detachable container. [See FIG. 10a, FIG. 10b and FIG. 10c].

The tapered sealing surface of each port comprises a lower portion that is cylindrical and of a first diameter, and an upper portion that begins with a bottom having the first diameter, which narrows or tapers to a second diameter that is narrower than the first diameter. The upper portion of each port may further comprise an upper cylindrical portion having the second diameter which is narrower than the first diameter and can be accommodated by a reciprocal arrangement of features on an air-water separating tank. The container inlet and container outlet port themselves may be of the same height, in which case the tapered sealing surface of one port, preferably the container outlet port comprises a tapered sealing surface that tapers to the second diameter at a lower point than does the tapered sealing surface of the other port, preferably the container inlet port. The container port in which the tapered sealing surface tapers to the second diameter at a lower point, preferably the container outlet port, will then comprise an upper cylindrical portion having the second diameter, the top of which port reaches the same height as the other port.

Alternatively, the container inlet and container outlet port themselves may be of different heights, in which case the container outlet port is preferably the shorter port. In such a case, the tapered sealing surfaces of both ports may have the same or different proportions, and the tapered surface of each port may reach the second, narrower diameter at different heights, or the same height in which case the tapered sealing surface of the container port which is taller, preferably the container inlet port, will then comprise an upper cylindrical portion having the second diameter.

In other aspects, the invention comprises a detachable container useful as a dental amalgam recycling container, said detachable container having an outside top mating surface comprising a container inlet port and a container outlet port, wherein each of the container inlet port and container outlet port comprises a flat sealing surface, such that, when the detachable container is aligned with and attached to an air-water separating tank of an amalgam separation apparatus, the flat sealing surface of the container inlet port forms an air-tight and water-tight seal with an air-water separator tank liquid effluent outlet and the flat sealing surface of the container outlet port forms an air-tight and water-tight seal with a further conduit means for liquid effluent discharge after solid amalgam has separated from the liquid effluent and collected at the bottom of the detachable container. [See FIG. 11a, FIG. 11b and FIG. 11c].

In these embodiments, the sealing surfaces may effectively complement or eliminate the need for O-rings in order to form an air- and water-tight seal. The sealing surface may be made of a material that is designed to provide an improved air- and water-tight seal, such as rubber, latex or other flexible or pliable material, the surface of which will deform or adapt to accommodate the shape of the contact points of another surface with which it is contacted.

In certain embodiments, the invention comprises a container, useful as a dental amalgam recycling container, comprising threads for attachment of a shipping cap. In certain embodiments, the dental amalgam recycling container further comprises two plugs held in place by said shipping cap and an O-ring fitted in an O-ring groove to prevent leaks. The dental amalgam recycling containers of the present invention may further comprise a two tier cap that enables people with hands of different sizes to grip the cap and tighten to achieve a very tight seal.

In certain embodiments, the invention comprises an adapter for an air-water separator tank, wherein the adapter enables a recycling container without compatible effluent ports to attach to an air-water separator tank. Said air-water separator tank may comprise, for example, a component of a dental amalgam recycling system, as described above. In certain embodiments, the adapter may comprise threads. In alternative embodiments, the adaptor may be without threads.

As described above, the potential for leakage exists in a collection canister such as the recycling container used in the dental amalgam recycling systems described herein. Such leakage may occur, for example, due to incorrect installation, or due to misalignment of a container and its intended mating partner, such as the air-water separation tank, or its intended cap, such as the shipping cap, which may cause O-rings to deform and/or seal irregularly. In order to address this problem, and/or further reduce the potential for leakage, a collection canister, such as a recycling container used in a dental amalgam recycling system, may have one or more 'keyways' cast into its outside top mating surface, and the intended mating partner, such as the air-water separation tank may have one or more corresponding 'key(s)' be cast into its mating surface, such that the key(s) and keyway(s) must be aligned in order for the collection canister (e.g., the recycling container) and its mating partner (e.g., the air-water separation tank; or the shipping cap) to mate properly. This key/keyway system can help ensure even pressure across the entire circumference of the O-ring surface on each port. Similarly, such key(s) and keyway(s) may be used to ensure proper replacement of the container and/or the air-water separation tank, such that incorrect replacement can be avoided or minimized.

In the present invention, the inventors have surprisingly found that, using the alignments and configurations described above for the detachable containers of the present invention, the above keys and keyways may be optimal, but are not a necessary element of the invention. Thus, in certain embodiments, the invention comprises a detachable container, suitable for mating securely with an air-water separation tank, said detachable container having an outside top mating surface comprising a container inlet port and a container outlet port that are asymmetrically aligned along a central axis across the diameter of the top mating surface; wherein one of the ports is situated closer to the center of the top mating surface, and the other port is situated closer to the outside of the top mating surface, such that the top mating surface may be aligned in a unique orientation with a dental amalgam air-water separating tank having a reciprocal arrangement of features to accommodate the top mating surface of the detachable container.

In certain embodiments the container inlet ports and container outlet ports each comprise an O-ring groove suitable for the insertion of an O-ring. In certain embodiments, the O-ring grooves are located at different heights from the top mating surface of the detachable container. The container inlet and container outlet port themselves may be of the same height, in which case the O-ring groove of one port is located at a lower point on the port, a further distance from the top of the taller port. In other embodiments, the container inlet and container outlet port themselves may be of different heights and the O-ring groove (24) may be located equally distant from the top of each of the ports.

Thus, the present invention comprises a detachable container suitable for mating securely with an air-water separation tank. The detachable container comprises a top mating surface, which comprises a container inlet port and a container outlet port. The two ports are asymmetrically located along a central axis defining a diameter of the top mating surface, with the first port located closer to the center of the top mating surface than the second port, and the second port located closer to an outer rim of the top mating surface.

The air-water separation tank comprises a bottom mating surface, said bottom mating surface further comprises a reciprocal arrangement of an effluent outlet port, and a conduit providing for discharge of liquid effluent from the detachable container after solid amalgam has collected at the bottom of the detachable container.

The reciprocal arrangement of the air-water separation tank's bottom surface permits alignment of the container inlet port with the effluent outlet port from the air-water tank, and alignment of the container outlet port with the conduit, such that the top mating surface of the detachable container can be mated securely with the bottom mating surface of said air-water separation tank upon such alignment of the top mating surface of the detachable container with the bottom surface of the air-water separation tank.

In certain embodiments of the invention, the container inlet port and container outlet port of the detachable container each comprise an O-ring groove to accommodate placement of an O-ring. In preferred embodiments, O-ring groove on the container inlet port may be located lower than the O-ring groove on the container outlet port.

In other embodiments of the invention, one or both of the container inlet port and the container outlet port of the detachable container comprise a tapered diameter, or a stepped diameter.

In other embodiments of the invention, one or both of the container inlet port and the container outlet port of the detachable container comprise a tapered sealing surface or a flat sealing surface.

In other embodiments of the invention, the top mating surface of the detachable container comprises an outer perimeter, and further comprises two retaining tabs extending outward from the outer perimeter. The retaining tabs are located at opposite ends of a central axis defining a diameter of the top mating surface, and the retaining tabs are sufficiently strong to be capable of supporting the weight of the detachable container.

In certain embodiments of the invention, the top mating surface of said detachable container further comprises an outer perimeter, and said detachable container comprises one or more keyways cast into the outer perimeter of its top mating surface. These one or more keyways may be aligned with one or more keys present on the bottom mating surface of an air-water separation tank to facilitate mating of the top mating surface of the detachable container to the bottom mating surface of the air-water separation tank.

1—Backplate
2—Waste Inlet (from dental practice)
3—Air/water Separator Top
4—Top Support Bracket
5—Air/Water Separation Tank
6—Suction tube 7—Air/Water Separator Base
8—Outlet Tube (To vacuum system)
9—Recycling Container Top Manifold
10—Lower Support Bracket
11—Restrictor
12—Detachable Recycling Container
13—Retaining Pins (2)
14—air-water separator tank effluent outlet port
15—recycling container inlet port
16—recycling container outlet port
17—recycling container threads
18—two tier recycling cap
19—O-ring groove
20—cap plugs
21—O-ring
22—container inlet or outlet port
23—container keyway
24—container O-ring groove
25—lower portion of container port
26—upper portion of container port
27—retaining tabs (2)

Figure 6:
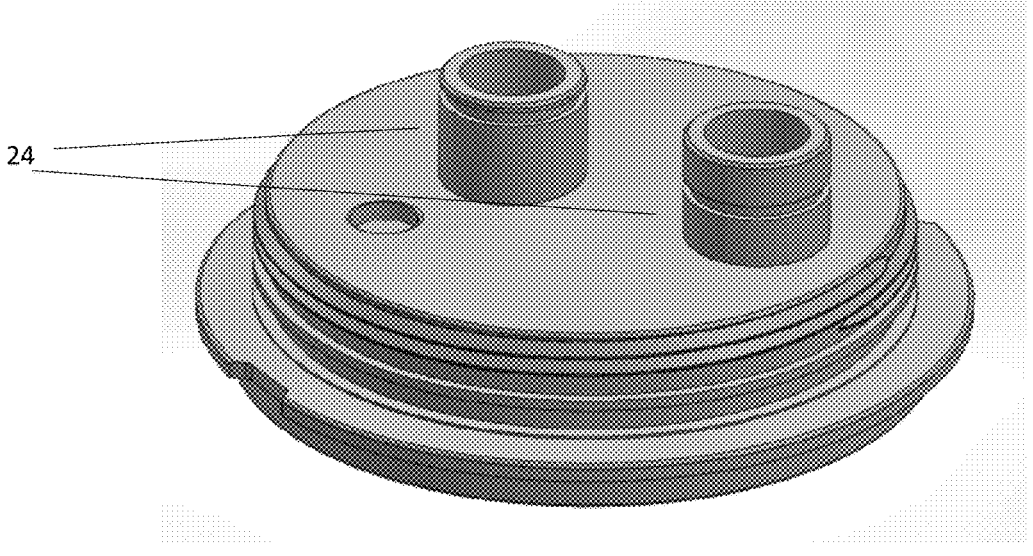

FIG. 6 is a schematic view of an embodiment of a detachable container according to the present invention, in which the inlet and outlet ports are the same height, and have O-ring grooves, which are fitted for the insertion of O-rings, at different heights.

Figure 7:
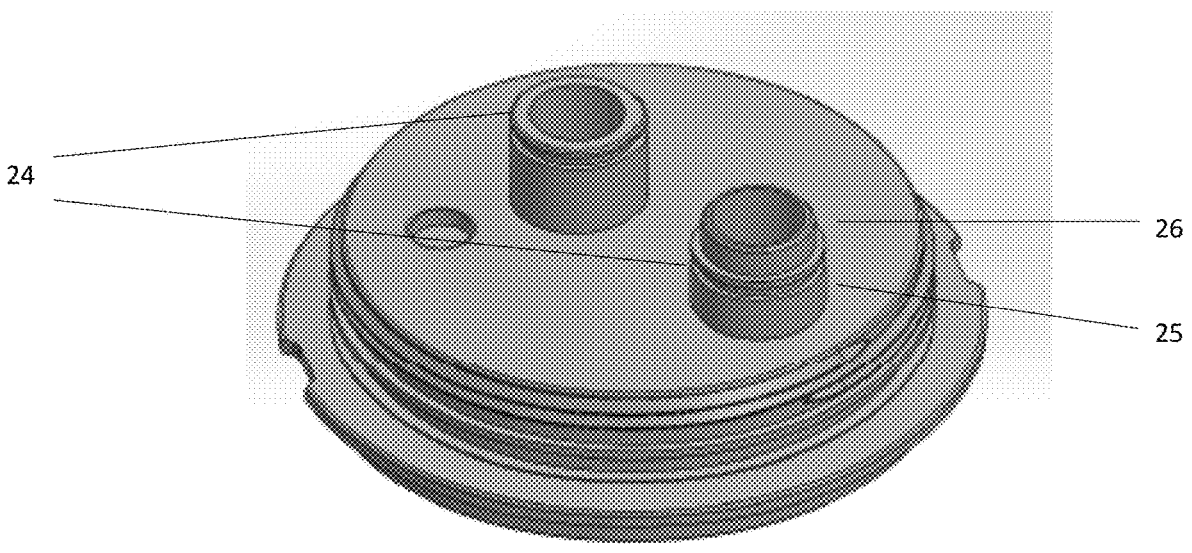

FIG. 7 is a schematic view of an embodiment of a detachable container according to the present invention, in which the inlet and outlet ports are the same height, and one of the ports comprises a stepped diameter.

Figure 8:
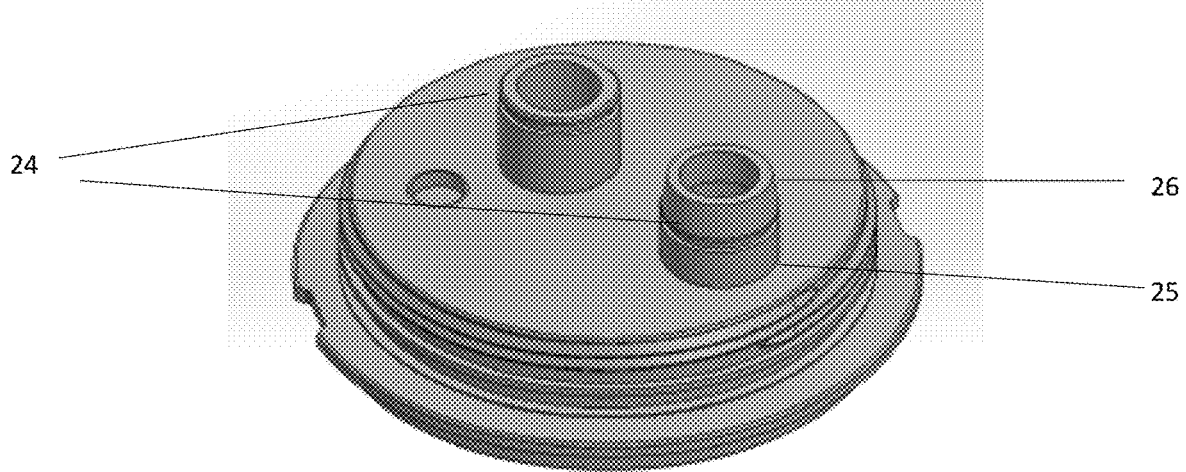

FIG. 8 is a schematic view of an embodiment of a detachable container according to the present invention, in which the inlet and outlet ports are the same height, and one of the ports comprises a tapered diameter, with a lower portion that is cylindrical and an upper portion that is tapered to a narrower diameter.

Figure 9:
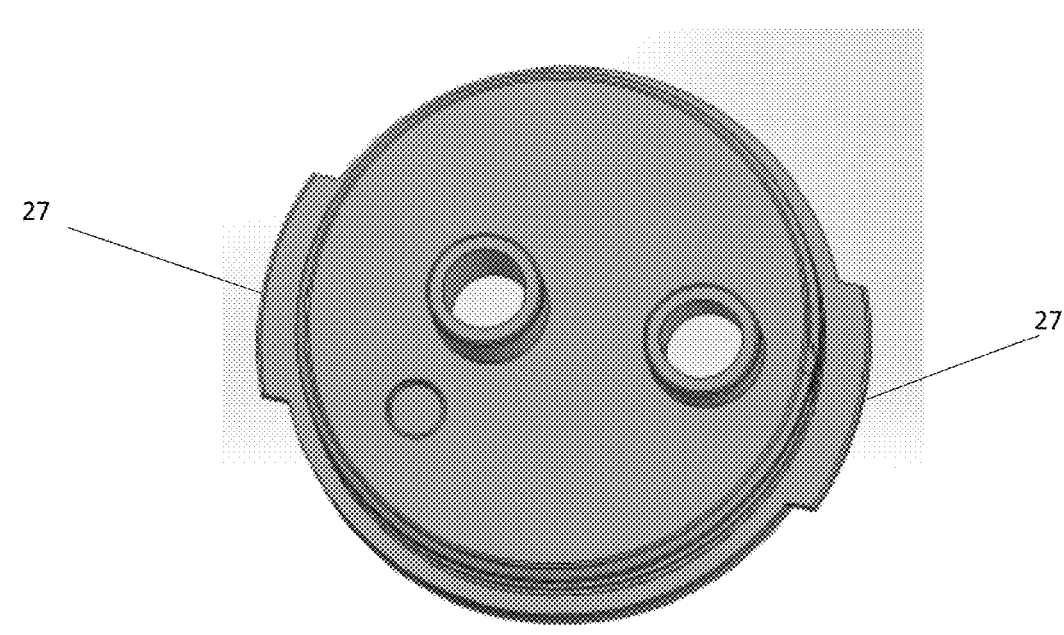

FIG. 9 is a schematic view of an embodiment of a detachable container according to the present invention, in which the outer rim of the outside top mating surface comprises two retaining tabs projecting outward from the container, the retaining tabs being located opposite from each other along the outer rim. The retaining tabs provide a surface or ridge under which retaining pins may be placed to add to the security of the detachable container.

Figure 10A:
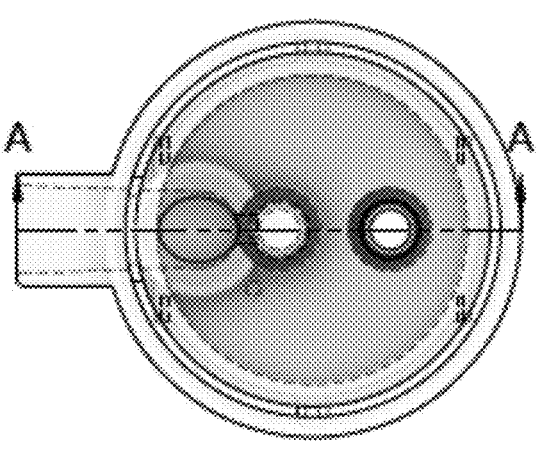
Figure 10B:
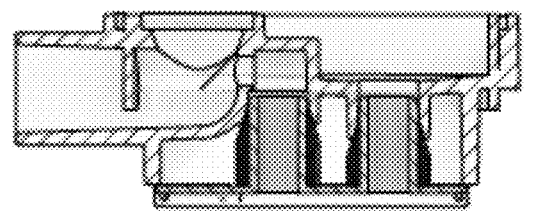
Figure 10C:
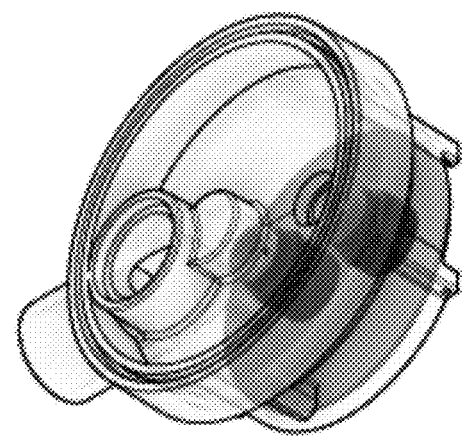

FIGS. 10a, 10b and 10c present three schematic views of an embodiment of a detachable container according to the present invention, in which the inlet and outlet ports each comprise a tapered sealing surface. FIG. 10a presents a top view; FIG. 10b presents a side-on view; and FIG. 10c presents an angled view.

Figure 11A:
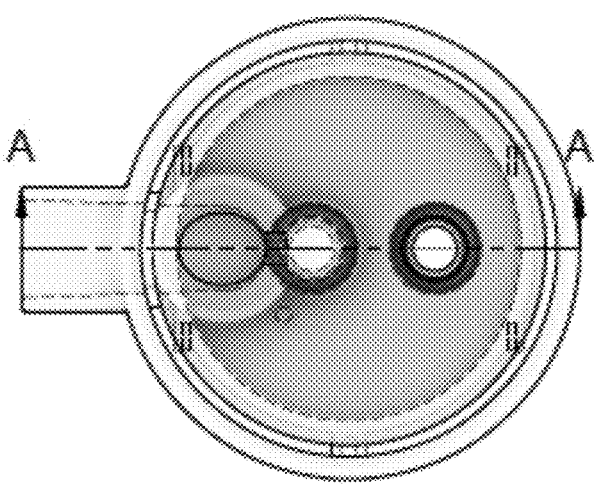
Figure 11B:
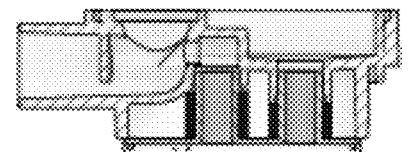
Figure 11C:
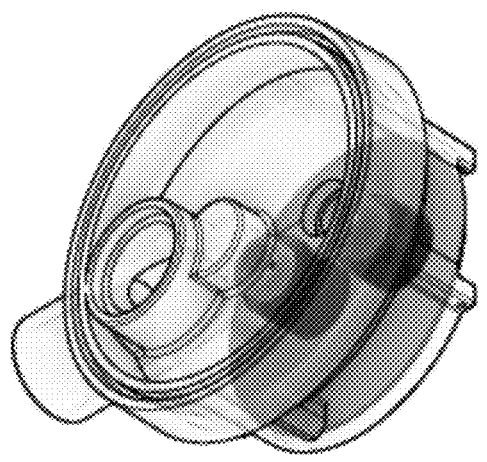

FIGS. 11a, 11b and 11c present schematic views of an embodiment of a detachable container according to the present invention, in which the inlet and outlet ports each comprise a flat sealing surface. FIG. 11a presents a top view; FIG. 11b presents a side-on view; and FIG. 11c presents an angled view.

Figure 12A:
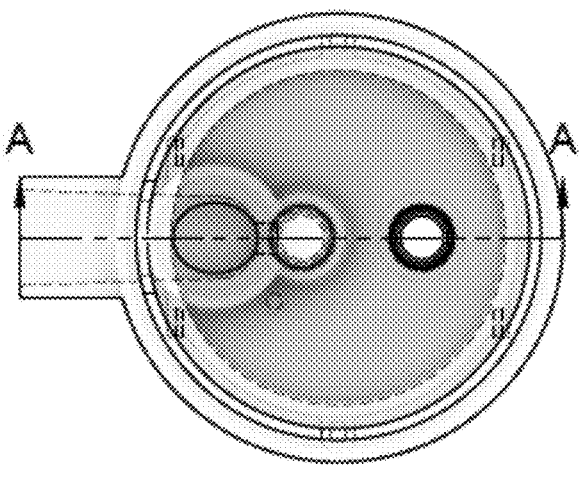
Figure 12B:
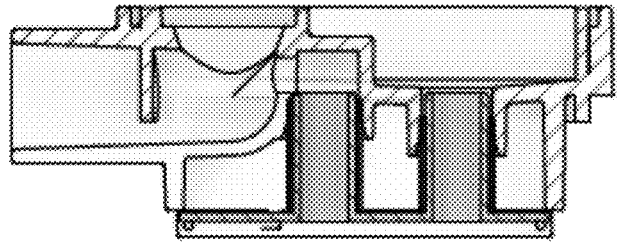
Figure 12C:
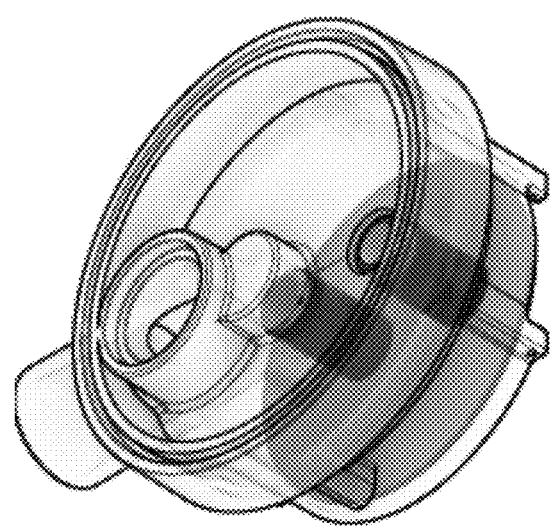

FIGS. 12a, 12b and 12c present three schematic views of an embodiment of a detachable container according to the present invention, in which the inlet and outlet ports each comprise an overmolded sealing surface. FIG. 12a presents a top view; FIG. 12b presents a side-on view; and FIG. 12c presents an angled view.

DETAILED DESCRIPTION WITH REFERENCE TO THE DRAWINGS

According to one aspect of the instant invention, an apparatus is provided for removing and recycling metal-containing particles and other waste particles from effluent, particularly effluent from a dental office. While herein the term "metal particles" may frequently be employed, it is contemplated that the apparatus is capable of separating other solid particles from effluent liquid.

According to one aspect of the invention, an apparatus for removing metal particles and other solid particles from liquid suction effluent can be installed in a dental office using a pre-existing suction/vacuum pump system. The apparatus may share a common vacuum pump with conventional dental chair suction apparatus, without interrupting the use of suction equipment at the dental chairs.

Removal of solid particles from liquid suction effluent is effected by sedimentation.

In accordance with one embodiment of the invention, the dental office suction effluent is passed from dental chair suction equipment outlets to an air water separator tank via a suitable inlet port for the tank. The air-water separator tank in turn passes effluent into a sedimentary deposit tank, closed on all sides when in use and preferably readily detachable for emptying or replacement.

In certain aspects of the instant invention the sedimentary deposit tank has a secondary function as a recycling container. In another aspect of the invention this recycling container can have features built in to make recycling easier and to reduce the amount of packaging and waste in the recycling system.

In another embodiment of the invention designed to minimize the space required to install the amalgam recycling system the air-water suction tube is internalized-within the air-water separator tank.

Figure 1:
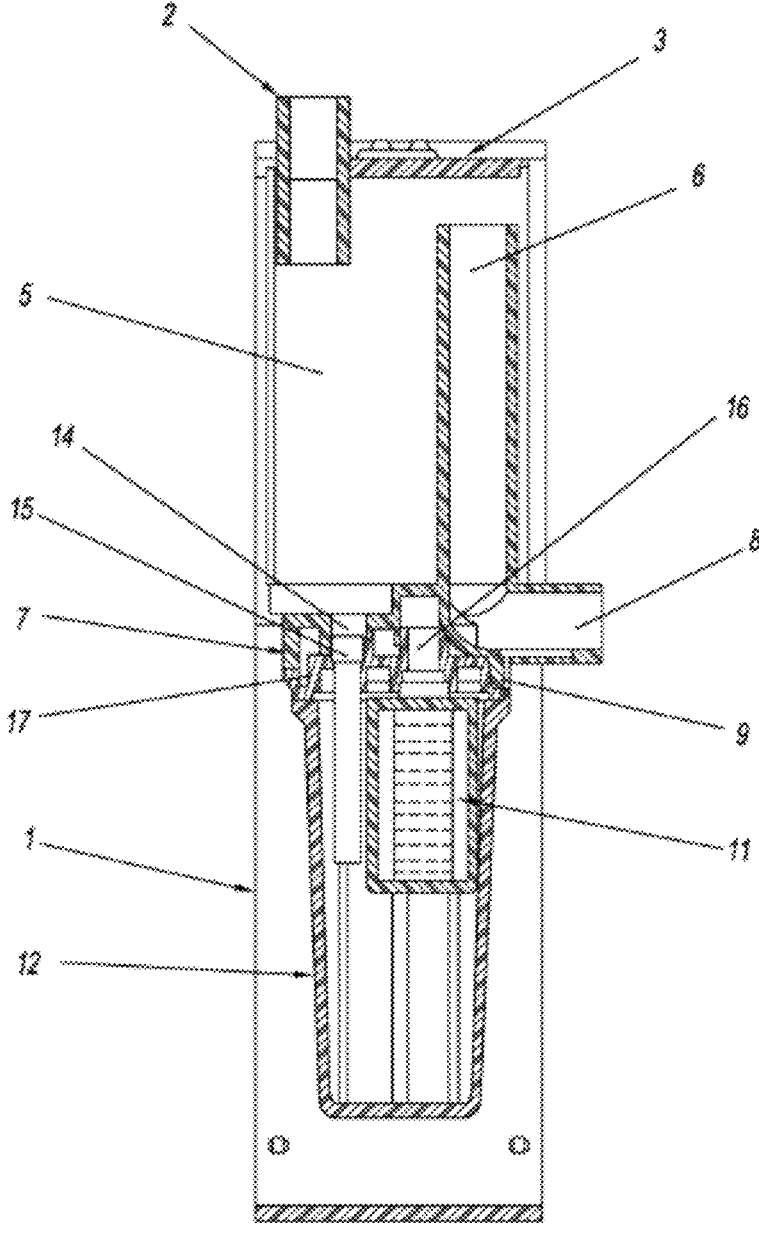
FIG. 1 is a schematic front view of an embodiment of particle removal and recycling apparatus according to the invention, for particular use in a dental office.
Figure 2:
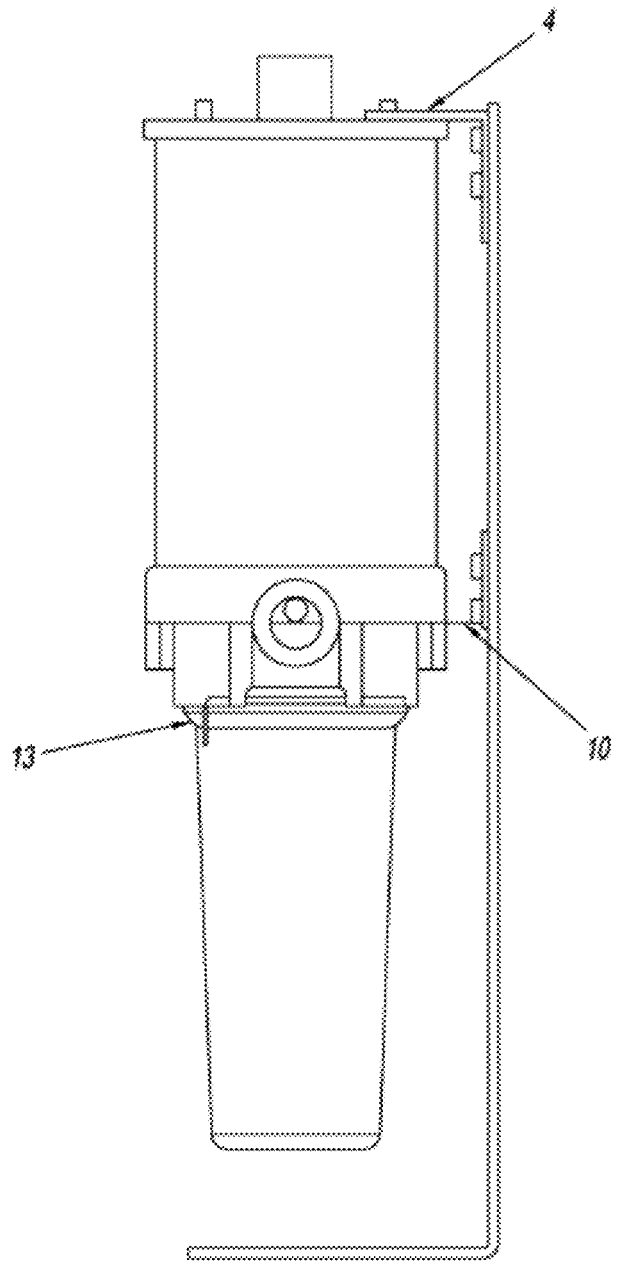
FIG. 2 is a schematic side view of an embodiment of particle removal and recycling apparatus according to the invention, for particular use in a dental office.

FIG. 1 and FIG. 2 shows two views of the separation apparatus according to the present invention in detail. Effluent from the dental chairs and a quantity of air are sucked through a suction apparatus exhaust conduit, through an air-water separator tank inlet 2, and thence into an air-water separator tank 5. The liquid effluent passes out of the air-water separator tank 5 via air-water separator tank outlet port 14, while air passes downstream via the air suction tube 6 while maintaining constant vacuum upstream of amalgam separator.

The air-water separator tank effluent outlet port 14 passes effluent by gravity out of the air-water separator tank 5 and into the detachable recycling container 12 through the recycling container inlet port 15 for target particle separation by sedimentation. Solids settle and accumulate in the bottom of Recycle container 12. Liquid content of waste flows primarily by gravity, although intermittently assisted by vacuum through Restrictor 11 which slows the flow rate of liquid to assist in sedimentation process and ultimately "clean" effluent discharge through the recycling container outlet port 16.

Outlet ports 16 and inlet port 15 can be a variety of shapes and sizes, square, oval (as depicted), round or even more unusual shapes like a star. Preferred ports are those that provide a tight seal, allow for easy removal, and do not break. Oval or round are preferred embodiments. Round are most preferred.

A vacuum at the outlet tube 8 is generated when the vacuum pump is operating, thereby sucking air out of the air-water separator tank 5 via suction tube 6 while maintaining vacuum upstream of amalgam separator apparatus. Effluent from the recycling container 12 passes through the restrictor 11 where remaining non-settable fine particles are removed from the effluent and into the recycling container outlet port 16 to be discharged from the apparatus via common outlet tube 8. Matter sucked by the vacuum pump, generally free of removed solids, is discharged via vacuum pump exhaust line into a municipal drain of the public sewage system.

The system is provided with a simple back plate 1 for easy dental office placement as well as removable retaining pins 13 to ensure the recycling container does not detach from the air-water separation tank 5 when there is no vacuum in the system.

In certain embodiments, the recycling container ports 16 and 15 may be different heights in order to aid in alignment of the detachable recycling container 12 in the air-water separator base 7. In a preferred embodiment, the outlet port 16 engages before the inlet port 15 while during removal the inlet port 15 disengages first. This causes a small volume of fluid to be pulled out of the collection container back into air-water separator tank 5 creating head space and eliminating upward force of vacuum which eases removal of recycle container 12 by operator. Existing devices require rocking, wiggling or applying extensive down force for removal of recycle container 12.

In one preferred embodiment of the invention designed to minimize recycling costs and waste, the recycling container/sedimentary deposit tank has threads 17 built into the container to enable the addition of a liquid tight top for shipping.

Figure 3A:
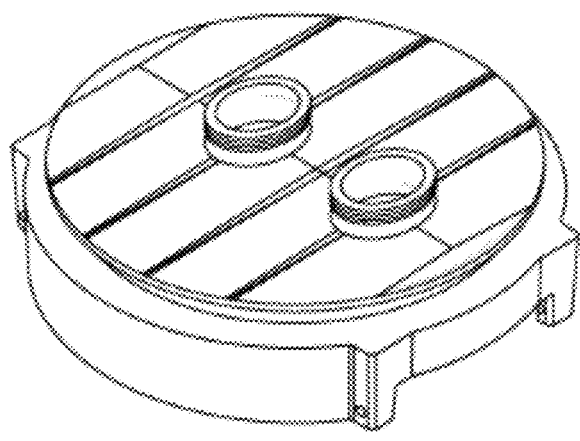
FIG. 3a is a schematic view of an embodiment of an universal adapter for fitting various different sized recycling containers to the air-water separator of the present invention.
Figure 3B:
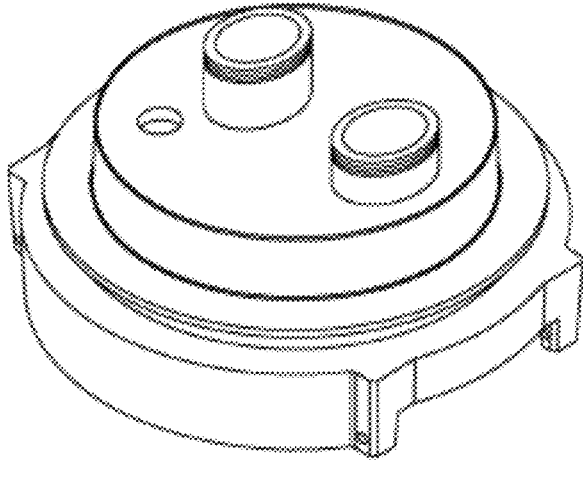
FIG. 3b is a schematic view of an alternative embodiment of an universal adapter for fitting various different sized recycling containers to the air-water separator of the present invention.

FIG. 3 shows a schematic diagram of an adapter according to the invention to enable the use of recycling containers from a variety of sources that are lacking in correctly shaped ports 16 and 15 or otherwise are unable to fit the air-water separator tank 5 according to the invention due to shape differences.

Figure 4A:
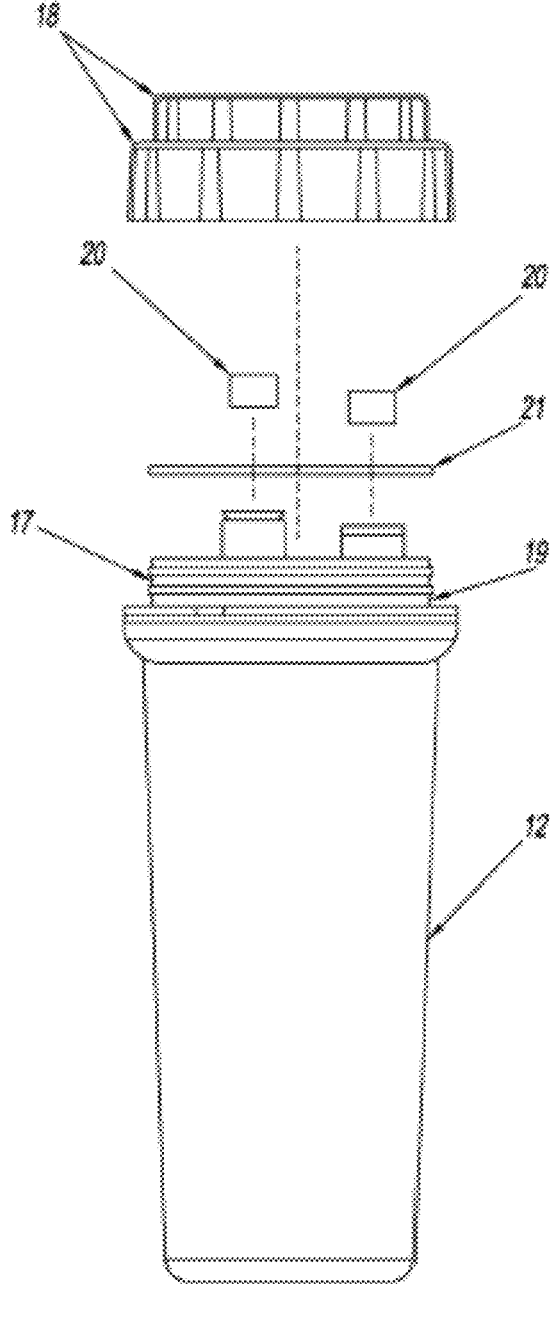
FIG. 4a is a schematic view of an embodiment of a recycling container and cap system of the invention.
Figure 4B:
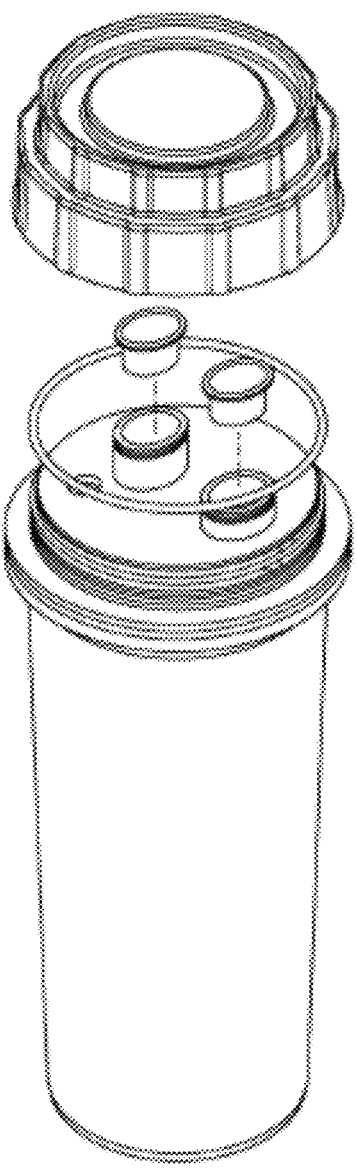
FIG. 4b is a schematic perspective depiction of an embodiment of a recycling container and cap system of the invention.
Figure 5A:
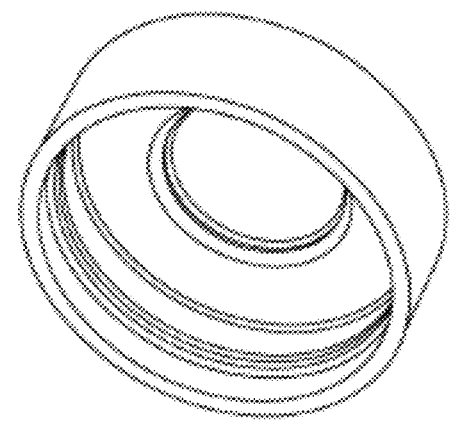
FIG. 5a is a schematic inside view of an embodiment of a recycling cap for the recycling containers of the invention.
Figure 5B:
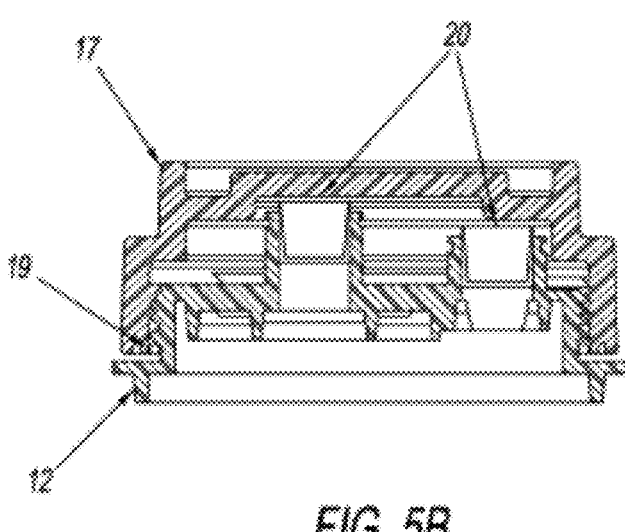
FIG. 5b is a schematic depiction of a recycling cap according to the invention fitting on a partial view of a recycling container according to the invention.

FIG. 4a shows a schematic diagram of the recycling container and cap system (see FIG. 5 for more cap 18 detail) according to the present invention. The cap 18 is a two tier shape to allow for a tight grip by both a big and smaller hand in order to achieve a strong seal as required by the invention. An O-ring 21 is provided and fits into an O-ring groove on the recycling container 12. Plugs 20 are used to provide a first leak proof seal for the recycling container 12. These plugs 20 are held in place by the cap 18 when the cap is threaded onto the recycling container as depicted in FIG. 5b.

FIG. 6 shows an embodiment of a detachable container according to the present invention, in which the inlet and outlet ports have O-ring grooves 24, which are fitted for the insertion of O-rings, are indicated.

FIG. 7 shows an embodiment of a detachable container according to the present invention, in which the O-ring grooves 24 are indicated, and wherein one of the ports comprises a stepped diameter, with the lower portion 25, and upper portion 26, indicated.

FIG. 8 shows an embodiment of a detachable container according to the present invention, in which the O-ring grooves 24 are indicated, and wherein one of the ports comprises a tapered diameter, with a lower portion 25 that is cylindrical and an upper portion 26 that is tapered to a narrower diameter are indicated.

FIG. 9 shows an embodiment of a detachable container according to the present invention, in which the outer rim of the outside top mating surface comprises two retaining tabs 27 projecting outward from the container, the retaining tabs being located opposite from each other along the outer rim. The retaining tabs are indicated.

FIGS. 10a-10c show three views of an embodiment of a detachable container according to the present invention, in which the inlet and outlet ports each comprise a tapered sealing surface.

FIGS. 11a-11c show three views of an embodiment of a detachable container according to the present invention, in which the inlet and outlet ports each comprise a flat sealing surface.

FIGS. 12a-12c show three views of an embodiment of a detachable container according to the present invention, in which the inlet and outlet ports each comprise overmolded sealing surfaces.

Generally, under present practice, the dental staff will not be able to remove deposited sediment from the recycle container nor remove accumulated particle residues from the restrictor unit themselves. Thus, it is desirable that such removal be done by a competent effluent residue processing facility. Therefore, under present practice, it is expected to be preferred that the recycling container with its enclosed restrictor unit be removed when full, or periodically replaced by fresh tanks from time to time as required. The spent tank with an accumulation of metallic and other particles can then be sent to a processing facility for proper disposal of the targeted metallic particles, such as mercury, and recovery of precious metals such as silver.

Although the sedimentary deposit process is effective to remove a satisfactorily high proportion of the target particles desired to be removed from the effluent, the recycling container desirably includes an outlet restrictor right in the chamber to catch any floating materials as well as any other materials that did not settle out.

If the recycle container is not changed as required or filled beyond normal capacity, waste liquid from dental practice may back up into air water separator tank. Should this occur, effluent overflows through the air suction tube and into the outlet port and is discharged into the vacuum pump draw line and thence eventually into the municipal drain. However, it is desirable that the system should operate in such a manner as to avoid having the air-water separator tank become completely full, since effluent exiting through the air outlet port will contain particles that will not be separated by the separator. If, however, such a by-pass condition occurs at no time will the suction generated by the vacuum pump be lost or interrupted at the dental office.

In a further embodiment of the invention oriented towards large-scale institutional applications, in which many dental chairs or other sources of effluent are connected to the same suction and drain services, several parallel-connected recycling containers and associated apparatus, each such composite apparatus including a air-water separator tank and preferably one, or alternatively two attached recycling containers, may be operated in parallel to provide sufficient treatment capacity for large effluent volumes.

All publications, web-sites, patents and patent applications cited in the specification are hereby incorporated herein by reference in their entirety for the disclosure for which they are cited.

Having read the above specification, other alternatives and variants of the above described methods and apparatus suitable for practicing the methods will occur to those skilled in the technology. Such alternatives, modifications and variants fall within the scope of the present invention.

The invention as described above also includes the following non-limiting claims, which describe particular embodiments of the invention.

The invention claimed is:

1. A detachable container suitable for mating securely with an air-water separation tank, said detachable container having a top mating surface comprising a container inlet port and a container outlet port wherein the two ports are asymmetrically located along a central axis defining a diameter of the top mating surface, with the first port located closer to the center of the top mating surface than the second port, and the second port located closer to an outer rim of the top mating surface, said air-water separation tank comprises a bottom mating surface, said bottom mating surface comprising a reciprocal arrangement of an effluent outlet port, and a conduit providing for discharge of liquid effluent from the detachable container after solid amalgam has collected at the bottom of the detachable container;

wherein said reciprocal arrangement permits alignment of the container inlet port with the effluent outlet port from the air-water tank, and alignment of the container outlet port with the conduit, such that the top mating surface of said detachable container can be mated securely with the bottom mating surface of said air-water separation tank upon such alignment of the top mating surface of the detachable container with the bottom surface of the air-water separation tank.

2. The detachable container of claim 1, wherein the container inlet port and container outlet port each comprise an O-ring groove to accommodate placement of an O-ring.

3. The detachable container of claim 2, wherein the O-ring groove on the container inlet port is located lower than the O-ring groove on the container outlet port.

4. The detachable container of claim 2, wherein one or both of the container inlet port and the container outlet port comprise a tapered diameter.

5. The detachable container of claim 2, wherein one or both of the container inlet port and the container outlet port comprise a stepped diameter.

6. The detachable container of claim 2, wherein one or both of the container inlet port and the container outlet port comprise a tapered sealing surface.

7. The detachable container of claim 2, wherein one or both of the container inlet port and the container outlet port comprise a flat sealing surface.

8. The detachable container of claim 1, wherein the top mating surface comprises an outer perimeter, and further comprises two retaining tabs extending outward from the outer perimeter, and wherein said retaining tabs are located at opposite ends of a central axis defining a diameter of the top mating surface, said retaining tabs being capable of supporting the weight of the detachable container.

9. The detachable container of claim 1 wherein the top mating surface of said detachable container further comprises an outer perimeter, and wherein said detachable container comprises one or more keyways cast into the outer perimeter of its top mating surface.

* * * * *